(12) United States Patent (10) Patent No.: US 6,914,153 B2
Morini et al. (45) Date of Patent: Jul. 5, 2005

(54) PROCESS FOR PREPARING ALKYLIDENE SUBSTITUTED SUCCINIC ACID ESTERS

(75) Inventors: Giampiero Morini, Padua (IT); Yuri Gulevich, Ferrara (IT); Marco Fachini, Padua (IT); Giansiro Prini, Rovigo (IT); Antonio Cristofori, Rovigo (IT)

(73) Assignee: Bassell Poliolefine Italia S.p.A., Milan (IT)

( * ) Notice: Subject to any disclaimer, the term of this patent is extended or adjusted under 35 U.S.C. 154(b) by 70 days.

(21) Appl. No.: 10/343,884

(22) PCT Filed: Jun. 4, 2002

(86) PCT No.: PCT/EP02/06097

§ 371 (c)(1),
(2), (4) Date: Feb. 5, 2003

(87) PCT Pub. No.: WO02/098837

PCT Pub. Date: Dec. 12, 2002

(65) Prior Publication Data

US 2003/0181743 A1 Sep. 25, 2003

(30) Foreign Application Priority Data

Jun. 7, 2001 (EP) ............................................ 01202184

(51) Int. Cl.$^7$ ............................................ C07C 67/343
(52) U.S. Cl. ....................................................... 560/76
(58) Field of Search ........................................... 560/76

(56) References Cited

FOREIGN PATENT DOCUMENTS

DE 800227 10/1950
EP 760355 3/1997 ........... C07C/13/32

OTHER PUBLICATIONS

C. G. Overberger et al., "The Preparation of 2-Alkyl-1, 4-butanediols;" *J. Am. Chem. Society*; vol. 71 (3618-21) 1949.

G. H. Daub et al., "The Stobbe Condensation with Sodium Hydride;" *J. Am. Chem. Society*; vol. 72 (501-4) 1950.

B. Wojcik et al., "Alkylation of Acetoacetic, Malonic and Succinic Esters," *J. Am. Chem. Society*; vol. 56 (2424-25) 1934.

N. R. Guirguis et al., "Synthesis of Enol Lactones of 3-Aroyl-2-(thienylmethylene)-propionic Acids and their Conversion into the Corresponding 4-Arylbenzo[b]thiophene-6-carboxylic Acids;" *Liebigs Ann. Chem.*; vol. 6 (1003-1011) 1986.

A. Basak et al., "Novel Regioselective Ester Hydrolysis by Pig-Liver Esterase;" *Bull. Chem. Soc. of Japan*; vol. 70 (2509-2513) 1997.

W. S. Johnson et al., "Organic Reactions;" *The Stobbe Condensation*; vol. VI, Chapter 1 (50-72) 1951; John Wiley & Sons Inc., NY.

H. Stobbe et al., "Die Dibenzalbernsteinsaure," *Ber.*, 37 (2240-2249) 1904 (German).

H. Stobbe, "Die Farbe der Fulgensauren und Fulgides," *Ber.*, 38 (3673-3682) 1905 (German).

Primary Examiner—Kamal A. Saeed

(57) ABSTRACT

A process for the preparation of alkylidene substituted succinates comprising a step (a) in which is carried out the reaction of a carbonilic compound, a succinic and a base in a reaction medium and a step (b) in which the alkylidene substituted product obtained in (a) is esterified, characterized in that the succinic ester is used in a molar amount substantially equal to, or lower than, the amount of compound carbonilic compound, (ii) the base is used in a molar amount substantially equal to the succinic ester and is selected from metal hydrides and metal and alkoxides, and (iii) the reaction medium comprises an aprotic liquid medium or a protic liquid medium having a Ka, measured in water, lower than that of iPrOH.

28 Claims, No Drawings

PROCESS FOR PREPARING ALKYLIDENE SUBSTITUTED SUCCINIC ACID ESTERS

This application is the U.S. national phase of International Application PCT/EP02/06097, filed Jun. 4, 2002.

The present invention relates to a novel process for preparing succinic esters substituted with unsaturated hydrocarbon groups in particular alkylidene groups. These compounds are convertible into alkyl substituted succinic esters that are used as electron donor compounds in the preparation of Ziegler-Natta heterogeneous catalysts for the polymerization of olefins. The transformation of alkylidene substituted succinates into alkyl substituted succinates is normally a clean reaction with an almost quantitative yield. Therefore, in order to industrially produce alkyl substituted succinates industrially exploitable, it is necessary to have an economically advantageous process for the production of alkylidene substituted succinic esters. By the term "economically advantageous" it is meant a process able to give the target product in good yields and acceptable purity by the use of such reagents and conditions that the process is as smooth and cheap as possible. This means that the most desirable processes are those in which mild conditions and short reaction times are used. Mono or dialkylidene substituted succinic esters are compounds known in the art. One of the methods for their preparation on a lab scale is the Stobbe reaction which involves the following scheme:

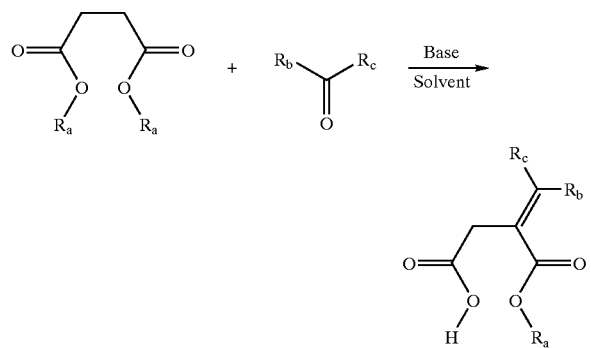

in which $R_a$ and $R_b$ are a C1–C20 hydrocarbon and $R_c$ is hydrogen or $R_b$. The so obtained emiesters can then be converted into the corresponding diesters via an esterification step. Over the time the Stobbe reaction has been used to prepare different types of alkylidene substituted succinic esters and in doing that the researchers selected, on a case by case basis, different conditions (bases, solvents, starting materials, reaction temperatures) in order to get the desired products. However, the original Stobbe and all the variations disclosed have such peculiarities that make them not particularly attractive from an industrial applicability standpoint. With respect to the preparation of mono alkylidene substituted succinic esters, the article from C. G. Overberg, C. W. Roberts, J. Am. Chem. Soc. (1949), 71, 3618–21 describes the preparation of several types of monoakylidene substituted succinic esters carrying out the Stobbe reaction using potassium tert-butoxide as a base and tert-butanol as a solvent. The starting diethyl succinate was used in excess with respect to both the starting ketone (25%) and the base, which in turn was in excess (about 10%) with respect to the ketone. The highest yields were obtained using acetone as a ketone and were 92% with respect to the ketone, but much lower with respect to the succinate (76%). Most importantly however, a long and complicate work-up (solvent distillation, acidification with diluted HCl to pH=3, complete solvent distillation, extraction with ether, extraction of the ethereal solution with basic water, acidification of basic water with HCl conc., extraction with ether, anhydrification, solvent evaporation) of the reaction was needed in order to separate the non-reacted reagents from the final product. This clearly would make such process very costly if carried out on a large scale. A similar situation was reported in G. H. Daub, W. S. Johnson, J. Am. Chem. Soc. (1950), 72, 501–4 where the solvent was benzene, the base sodium hydride and the starting ketone was benzophenone or acetophenone. Also in this case the yields were high with respect to the ketone (97%) but much lower with respect to the succinate (32%), thereby requiring demanding work-up of the reaction to isolate a final product of acceptable purity. More recently, EPA 760,355 disclosed the preparation of a monoalkylidene substituted succinate via the Stobbe reaction and using cycloheptanone as starting ketone. The base was potassium tert-butoxide and the solvent was dimethylformamide (DMF). Again, the yields were high with respect to the ketone (97%) but lower with respect to the succinate (75%), which was used in excess (34%). Taking also into account the excess of base used it is possible to understand that also in this case the work-up of the reaction in order to obtain only the desired product would be troublesome on a large scale. It is therefore apparent that the skilled in the art believed that, in order to obtain good yields, in the Stobbe reaction one should use an excess of succinate and base with respect to the ketone. This belief was confirmed also in the use of the Stobbe reaction for the preparation of alkylidene disubstituted succinic acids starting from unsubstituted succinates. It is worth noting that for this particular aspect the possibility of avoiding the intermediate work-up and separation step for the isolation of the monoalkylidene substituted ester is particularly attractive because it would greatly simplify an otherwise costly process. Stobbe himself described (H. Stobbe, P. Naum, Ber. (1904), 37, 2240–9; H. Stobbe, Ber. (1905), 38, 3673) an attempt to prepare alkylidene disubstituted succinic acids by using only one step. He therefore used an about double molar amount of base (sodium ethoxide) and ketone (acetone) with respect to the succinate in the presence of diethylether as solvent and at low temperature (−10° C.). Notwithstanding the very long reaction time (several days) the overall yields were so low (35–40%) that an heavy work up would be needed for separating the alkylidene disubstituted succinic acids from the non-reacted unsubstituted succinate.

In an article from B. Wojcik, H. Adkins, J. Am. Chem. Soc. (1934), 56, 2424–5 the Stobbe attempt was replicated at a higher temperature but the results were even worse, because the target product was not obtained and only the monoalkylidene substituted ester was produced in low yields. In view of the above, it would be of particular significance to discover the proper conditions under which a Stobbe type reaction can be carried out in order to obtain a final desired product with such yields that the process does not require a difficult work-up or separation step. The applicant has now discovered that such a desired process is feasible when certain conditions regarding starting products and ratio of reactants are observed.

It is therefore an object of the present invention a process for the preparation of succinates substituted with unsaturated hydrocarbon groups comprising a step (a) carried out in the presence of a reaction medium and a base in which a compound of formula (I)

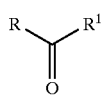

wherein R is a C1–C20 hydrocarbon group, $R^1$ is hydrogen or R, and $R^1$ and R can be linked together, with the proviso that when $R^1$ is hydrogen, R is a C4–C20 hydrocarbon group, is reacted with a compound of formula (II)

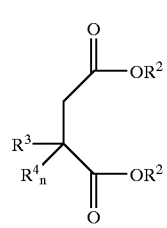

wherein $R^2$ is a C1–C20 hydrocarbon group, $R^3$ is hydrogen, a C1–C20 hydrocarbon group or an alkylidene group of formula $RR^1C=$, where R and $R^1$ have the same meaning as above, $R^4$ is hydrogen or a C1–C20 hydrocarbon group, n is 0 or 1, with the proviso that when $R^3$ is an alkylidene group of formula $RR^1C—$, n is 0, and a step (a) in which the alkylidene substituted product obtained in a step (a) is esterified; said process being characterized by the fact that step (a) is carried out under conditions such that (i) the compound of formula (II) is used in a molar amount substantially equal to, or lower than, the amount of compound (I), (ii) the base is in a molar amount substantially equal to the compound of formula (II) and is selected from hydrides of formula $MeH_z$ where Me is a metal belonging to group I–II of the periodic table of elements and z is the valence of the metal and alkoxides of formula $R^5OMe$ where $R^5$ is a C1–C15 hydrocarbon group and Me has the meaning given above, and (iii) the reaction medium comprises an aprotic liquid medium or a protic liquid medium having a $K_a$, measured in water, lower than that of i-PrOH. According to the present invention by the term "a molar amount substantially equal" is meant an amount which is no more than 10%, preferably 5%, by mol different from the amount of the compound of reference. As mentioned above, the preferred succinates substituted with unsaturated hydrocarbon groups are the alkylidene substituted succinates that in general are also the compounds obtainable in higher yields from the Stobbe reaction. The preferred reaction media are the aprotic diluents and, among them, toluene, ethylbenzene, xylene, dimethylformammide (DMF), N,N-dimethylacetamide, 1-methyl-2-pyrrolidone, diethylether, tetrahydrofurane are particularly preferred. Toluene and DMF are especially preferred and DMF is most preferred. Among protic solvents tert-butanol is one of the most preferred. According to the present invention, the reaction medium chosen among aprotic liquid medium or a protic liquid medium having a $K_a$, measured in water, lower than that of i-PrOH, should be the largely prevailing medium but may be not the only one. This means that small amounts (generally not higher than 10% by volume with respect to the total amount of the diluents) of liquids not falling within the above classes can in some cases be present for particular purposes. In particular, one of these liquids is preferably ethanol.

The base is preferably selected among alkoxides of formula $R^5OMe$ where $R^5$ is a C1–C15 hydrocarbon group and Me has the meaning given above. Particularly preferred among them are the alkoxides in which $R^5$ is a C1–C5 alkyl group and Me is Na or K. Especially preferred compounds are potassium tert-butoxide, sodium tert-butoxide, potassium ethoxide, sodium ethoxide. As a preferred aspect, such preferred alkoxides are used in combination with the aprotic solvents specified above. In particular the combination of the preferred alkoxides with the aprotic solvents like DMF or toluene is especially preferred.

As it has been explained, the above process is very suitable for obtaining the alkylidene substituted succinates in very high yields. Moreover, the applicant found that by carrying out the process according to the above-mentioned conditions the work-up of the final reaction mixtures is very simple. In fact, in most of the cases the work-up comprises only a dilution of the reaction mixture with water and an extraction of the desired products with an appropriate organic solvent, which is then suitably removed. One class of preferred starting compounds among those of formula (I) is that in which $R^1$ is hydrogen and R is selected from C4–C20 hydrocarbon groups, preferably from those not having unsaturation on the carbon atom linked to the carbonyl of formula (I). Among them, particularly preferred are the compounds in which R is a secondary or tertiary alkyl group. Another class of preferred compounds among those of formula (I) is that in which both R and $R^1$ are C1–C20 hydrocarbon groups preferably not having unsaturation on the carbon atom linked to the carbonyl of formula (I). Among them particularly preferred are the compounds in which R and $R^1$ are C1–C8 alkyl groups or alkylene groups linked together to form cyclic ketones. Examples of suitable ketones are methyl ethyl ketone, methyl n-propyl ketone, cyclobutyl methyl ketone, 3-buten-1-yl methyl ketone, acetylcyclopropane, diethylketone, methoxyacetone, isopropyl methyl ketone, 2-hexanone, 4-methyl-2-pentanone, methyl sec-butyl ketone, methyl tert-butyl ketone, ethyl propyl ketone, ethyl iso-propyl ketone, iso-amyl methyl ketone, 4-methyl cyclohexanone, 2-methylcyclohexanone, 3-methylcyclohexanone, 2,2-dimethyl-3-pentanone, 2-heptanone 3-heptanone, di-n-propyl ketone, dicyclopropyl ketone, di-iso-propyl ketone, neo-pentyl methyl ketone, 1-cyclopentyl-ethanone, 4-methyl-3-hexanone, 1-methyl-n-butyl methyl ketone, 3-ethyl-2-pentanone, isopropyl n-propyl ketone, 3-methyl-5-hexanone. The compounds in which both R and $R^1$ are the same and chosen among methyl, ethyl or propyl are preferred. Also preferred are the compounds in which R and $R^1$ are alkylene groups linked together to form cyclic ketones like cyclopentanone, cyclohexanone, or cycloheptanone. In carrying out step (a) of the above-specified process the reactants can be brought into contact with each other according to any order whatsoever. It constitutes a preferred embodiment, however, the addition of a solution of the base dispersed in the reaction medium to a mixture comprising the compounds (I) and (II) dispersed in another aliquot of the reaction medium. The temperature for carrying out the step (a) is not critical. It generally ranges from about −30 to 150° C., more typically from 0 to 110° C. and preferably from 20 to 80° C. The skilled in the art can easily select, within these ranges, the optimum temperature by taking into account parameters like the boiling temperature of the reaction medium, that of the starting compounds and the like. In view of the type of reagents involved in the Stobbe reaction, the product of step (a) has at least one of the carboxylic groups not esterified. In order to transform it in a completely esterified product an esterification step must be carried out which is the step (b) of the process of the invention. The esterification step can be carried out according to any of the many methods known in the art. One of the known methods for obtaining esters includes for example the esterification of a carboxylic acid through the reaction with an alcohol catalyzed by an acid or a base. A comprehensive review of many methods for preparing the esters can be found in *Organic Functional Group Preparation, II Edition, Academic* Press 1983. The preferred method for carrying out the esterification according to the present invention is the reaction of the product of step (a) (the emiester) with a compound of formula $R^6X$ where X is halogen and $R^6$ is C1–C20 hydrocarbon group. Preferably, X is selected from Br, Cl and I and $R^6$ is a primary C1–C8 alkyl group. Particularly preferred R6 groups are methyl, ethyl, propyl, n-butyl and iso-butyl. The use of ethyl bromide is especially preferred. This method has the advantage that the alkylidene substituted product of step (a) can directly be reacted with the compound of formula $R^6X$ without being first subjected to a preliminary work-up thereby saving time and increasing the yields. The temperature for carrying out step (b) is not critical. It generally ranges from about −30 to 150° C., more typically from −10 to 110° C. The skilled in the art can easily select, within these ranges, the optimum temperature by taking into account parameters like the boiling temperature of the reaction medium, that of the starting compounds and the like. As mentioned above, the alkylidene-substituted succinates can be converted into alkyl substituted succinic esters that are used as electron donor compounds in the preparation of Ziegler-Natta heterogeneous catalysts for the polymerization of olefins. Such a conversion may be suitably obtained via the catalytic hydrogenation. Also this reaction is very known in the art. A review of this kind of reaction can for example be-found in *Comprehensive Organic Transformation: a guide to functional group preparation* by R. C. Larock published by VCH Publishers. Among the various kinds of catalysts that can be used for carrying out this reaction, particularly preferred are the palladium or platinum deposited on carbon (Pd/C or Pt/C). The Pd/C containing 5% of Pd (Pd/C 5%) is particularly preferred. Also usable is the Ni Raney catalyst. The temperature at which this reaction is carried out may range from 0 to 150° C., more typically from 40 to 120° C. The hydrogen pressure is generally higher than the atmospheric pressure and preferably higher than 15 bar. The skilled in the art can easily select, within these ranges, the optimum temperature by taking into account parameters like the boiling temperature of the reaction medium, that of the starting compounds and the like. The reaction times for either of the above step cannot be foreseen. As a general indication the reaction time for these step may be from about 1 min to about 10 hours. More conveniently however, the reaction time is comprised from about 10 min to about 5 hours. In any case, the skilled in the art, can control the state of the reaction by following the techniques known in the art and decide when and to stop it. As explained above this process is very attractive from an industrial standpoint because it allows to obtain the desired product in very good yields and with a minimal work-up. The process of the present invention is also very versatile. Depending on the compound (II) that is used as starting material and on the conditions used, it allows the preparation of alkylidene monosubstituted esters, dialcylidene disubstituted succinic esters or monoalkylidene disubstituted succinic esters.

An example of alkylidene substituted succinic esters obtainable with the process of the invention are those of formula (III) below:

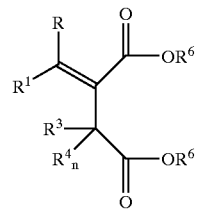

Wherein R, $R^1$, $R^3$, $R^4$ and $R^6$ have the same meanings as above.

One subclass of compounds of formula (III) obtainable with the process of the invention are those in which both $R^3$ and $R^4$ are hydrogen. Among those, specific preferred compounds obtainable are diethyl sec-butylidenesuccinate, diethyl cyclopropylidenesuccinate diethyl cyclohexylidenesuccinate, diethyl benzylidenesuccinate, diethyl cyclohexylmethylidenesuccinate, diethyl isobutylidenesuccinate, diethyl isopropylidenesuccinate, diethyl isopentylidenesuccinate and the corresponding products esterified with different alkoxy moieties. In order to obtain said products, step (a) of the present invention is carried out choosing compounds of formula (II) in which both $R^3$ and $R^4$ are hydrogen. The compound of formula (I) will be suitably selected on the basis of the type of alkylidene group to be introduced. Preferably, R and $R^1$ groups are such as they form compounds of formula (I) chosen among acetone, cyclohexanone, cyclopentanone, cyclohexylmethyl aldehyde. Also suitable are the following ketones: methyl ethyl ketone, methyl n-propyl ketone, cyclobutyl methyl ketone, 3-buten-1-yl methyl ketone, acetylcyclopropane, diethylketone, methoxyacetone, isopropyl methyl ketone, 2-hexanone, 4-methyl-2-pentanone, methyl see-butyl ketone, methyl tert-butyl ketone, ethyl propyl ketone, ethyl isopropyl ketone, iso-amyl methyl ketone, 4-methyl cyclohexanone, 2-methylcyclohexanone, 3-methylcyclohexanone, 2,2-dimethyl-3-pentanone, 2-heptanone 3-heptanone, di-n-propyl ketone, dicyclopropyl ketone, di-iso-propyl ketone, neo-pentyl methyl ketone, 1-cyclopentyl-ethanone, 4-methyl-3-hexanone, 1-methyl-n-butyl methyl ketone, 3-ethyl-2-pentanone, isopropyl n-propyl ketone, 3-methyl-5-hexanone.

In carrying out the reaction preferred solvents are DMF and toluene, while the preferred base can be selected from EtOK, EtONa, t-BuOK, t-BuONa.

Another subclass of compounds of formula (III) obtainable with the process of the invention are the di or trisubstituted succinic esters. The process of the invention can give dialkylidene disubstituted succinic esters and monoalkylidene di or trisubstituted succinic esters.

Dialkylidene disubstituted succinic esters can for example be prepared by using a monoalkylidene substituted succinic ester as the starting compound of formula (II). Alternatively, the starting succinic ester is a compound of formula (II) in which n is 1 and both $R^3$ and $R^4$ are hydrogen. Particularly preferred are diethyl succinate and diisobutyl succinate. The compound of formula (I) will be suitably selected on the basis of the type of alkylidene group to be introduced. Preferably, R and R1 groups are such as they form compounds of formula (I) chosen among acetone, cyclohexanone, cyclopentanone, (cyclohexylmethyl aldehyde). Acetone is the most preferred. After the completion of the step (a) and (b) the so obtained monoalkylidene substituted succinate is subject to an additional reaction step (a2) by contacting it with an equal or higher molar amount of compound of formula (I) in the presence of the base, thereby obtaining a reaction product which is then subject to an additional esterification step (b2).

The compound of formula (I) used in step (a2) can be the same as, or different from, the compound of formula (I) used in step (a). Preferably the same compound of formula (I) is used in both step (a) and (a2) and it is preferably selected from the group consisting of acetone, cyclohexanone, cyclopentanone, (cyclohexylmethyl aldehyde) and more preferably is acetone. Also the base can be the same as, or different from, that used in step (a). It is preferably selected among the alkoxides of formula $R^5OMe$ in which $R^5$ is a C1–C5 alkyl group and Me is Na or K. Especially preferred compounds are potassium tert-butoxide, sodium tert-butoxide, potassium ethoxide, sodium ethoxide. Also in step (a2) the base is preferably used in a substantially equimolar effective amount with respect to the alkylidene substituted compound. With the term effective amount we mean that the amount of the base introduced should be equimolar to the alkylidene substituted compound once the corresponding molar amounts of other possible compounds reacting with the base have been subtracted. As explained above, such preferred alkoxides are preferably used in combination with the aprotic liquid compounds used as reaction medium. Specifically, the reaction medium, which is preferably the same in all the steps (a), (b), (a2) and (b2), is selected from DMF or toluene. It is particularly interesting to note that all the above steps can be carried out in sequence without the need of any intermediate separation step. Also in this case the work-up of the reaction mixture is very simple. Dilution with water and extraction with organic solvents are the basic step for the work-up. Among the many organic solvents usable in the work-up, methyl tert-butyl ether, toluene, hexane and heptane are the most preferred.

When monoalkylidene di or trisubstituted succinic esters are to be prepared, the compound of formula (II) is suitably selected among those in which n is 1 and at least one of $R^3$ and $R^4$ is selected from C1–C20 hydrocarbon groups. Preferred compounds to be prepared are the monoalkylidene disubstituted succinic esters and therefore preferred starting compound of formula (II) are those in which $R^4$ is hydrogen and $R^3$ is a C1–C10 hydrocarbon group and, more preferably a C1–C6 alkyl or cycloalkyl group. It has been already explained that in general the so obtained alkylidene substituted esters are then converted into the corresponding saturated compounds via the conventional hydrogenation reaction. The saturated succinates find various applications in the art including the use in the pharmaceutical industry and, as mentioned above, as modifying compounds of Ziegler-Natta polymerization catalysts. The following examples are given in order to illustrate and not limit the invention.

EXAMPLES

Characterization

The characterization of the products obtained in the following examples has been carried out via $^1$H-NMR.

Example 1

Synthesis of 2-isopropylidene succinic acid, 1-ethyl ester

In a 250 mL round bottom flask 112 mmol of acetone and 102 mmol of diethyl succinate are added to 43 mL of N,N-dimethylformamide (solution A). In another 100 mL round bottom flask 103 mmol of potassium tert-butoxide are suspended in 35 mL of N,N-dimethylformamide, then 103 mmol of ethanol are added dropwise to the slurry at 20° C. A yellow solution is obtained (solution B). The solution B is then added to solution A dropwise in 22 minutes at 40° C. The obtained mixture is stirred 10 hours (reaction time) at 60° C. The reaction mixture is then allowed to cool down to room temperature and 280 mL of water is added. The aqueous solution is extracted with 250 mL of pentane. The aqueous layer is acidified to pH=1 with concentrate HCl and extracted with 250 mL of ether. Then the solvent is evaporated to give the mixture of crude products isomers (95% of yield).

Example 2

Synthesis of 2-isopropylidene succinic acid, diethyl ester

In a 1 L round bottom flask 650 mmol of acetone and 601 mmol of diethyl succinate are added to 250 mL of N,N-dimethylformamide (solution A). In another 500 mL round bottom flask 601 mmol of potassium tert-butoxide are slurred in 200 mL of N,N-dimethylformamide, then 601 mmol of ethanol are added dropwise to the slurry at 0° C. A yellow solution is obtained (solution B). The solution B is then added to solution A dropwise in one hour at 60° C. The obtained mixture is stirred 90 minutes (reaction time) at 60° C. Then at 60° C. 691 mmol of ethylbromide are added dropwise in 15 minutes and the mixture stirred for one hour (esterification time) at 80° C. The reaction mixture is then allowed to cool down to room temperature and transferred to a flask containing 510 g of ice. The aqueous solution is allowed to heat up to room temperature, extracted three times with 200 mL of pentane. The organic layer is then separated and washed two times with 750 mL of water, the solvent evaporated to give 118.46 g. of a mixture of crude product isomers (92% of yield).

Example 3

Synthesis of 2-(2-ethyl-hexylidene) succinic acid, diethyl ester

The same procedure described in Example 2 was repeated with the difference that 2-ethyl-hexanal was used instead of acetone. Moreover, the reaction time was 2 hours and 30 minutes, the esterification reaction lasted 1 hour 30 minutes. By adopting the same work-up operation, 132 g of a mixture of crude product isomers were obtained (77% of yield).

Example 4

Synthesis of 2,3-bis-(2-ethythexylidene) succinic acid, diethyl ester

The same procedure described in Example 3, was repeated with the difference that 2-(2-ethylhexylidene) succinic acid, diethyl ester was used as starting material instead of diethyl succinate. At the end, 202 g of crude product isomers were obtained (85% of yield).

Example 5

Synthesis of 2-isopropylidene succinic acid, diethyl ester 52.5 mmol of potassium ethoxide were suspended in 100 mL of N,N-dimethylformamide in a 250 mL round bottom flask. To this slurry, heated up to 60° C., a mixture of 50 mmol of diethyl succinate and 57.5 mmol of acetone was added dropwise in 10 minutes. The course of the reaction was detected by GC. After 60 minutes the reaction was completed with a conversion of 97.2% (determined by GC). Then 87.5 mmol of ethyl bromide were added to the reaction mixture at 60° C. The slurry was stirred for 60 minutes at 60° C. The reaction was complete, giving the product isomers with a yield of 95% (determined by GC).

Examples 6–7

Synthesis of 2-isopropylidene-succinic acid, diethyl ester

The procedure described in example 5 was followed using the specific reaction conditions reported in the table below.

| | | Stobbe condensation | | | | Esterification | | |
|---|---|---|---|---|---|---|---|---|
| Ex. | Solvent | Base | Time | T (° C.) | Conversion | Yield | T (° C.) | Time | Other |
| 6 | DMF | EtONa | 30' | 60 | 92 | 81.2 | 60 | 120' | |
| 7 | Toluene | EtONa | 180' | 110–96 | 90 | 84.2 | 90 | 120' | TBAB (cat.) |

TBAB = tetrabutylammoniumbromide 10% molar ratio with respect to the succinate
DMF = N,N-dimethylformamide,

Example 8

Synthesis of 2,3-diisopropylidene succinic acid, diethyl ester

In a 5 L jacketed reactor 2.6 mol of acetone and 2.4 mol of diethyl succinate were added to a mixture of 1 L of N,N-dimethylformamide (solution A). In a 1 L round bottom flask 2.4 mol of potassium tert-butoxide are slurried in 800 mL of N,N-dimethylformamide, then 2.4 mol of ethanol are added dropwise to the slurry at 0° C. A yellow solution is obtained (solution B). The solution B is then added to solution A in one hour at 60° C. The obtained mixture is stirred one hour at 60° C. Then, at 60° C., 2.76 mol of ethylbromide are added dropwise in 30 minutes and the mixture stirred for 90 minutes at 60° C. Then, 2.6 mol of acetone and another batch of freshly prepared solution B (using 800 mL of N,N-dimethylformamide, 2.76 mol of ethanol, 2.76 mol of potassium tert-butoxide) were added at 60° C. The reaction mixture was stirred for one hour at 60° C. After this period 2.76 mol of ethylbromide were added in 30 minutes and the obtained slurry stirred for 90 minutes at 80° C. The reaction mixture was then cooled down to 10° C, 2 L of water and 800 mL of methyltert-butyl ether were added. The aqueous layer was separated and extracted two times with 1.2 L of methyltert-butyl ether. The organic layer was then separated and washed three times with 1 L of water, the solvent evaporated to give after distillation, 555.5 g of crude product isomers (91% of yield).

Examples 9–11

Synthesis of Diethyl Esters of 2,3-Disubstituted-succinic acids

The same procedure described in Example 8 has been repeated using different ketones or aldehydes as starting materials. The obtained results are reported in the table below. The yield is calculated after distillation of the products.

| Ex. | Ketone/Aldehyde | Amount (g) | Yield (%) |
|---|---|---|---|
| 9 | 2-Butanone | 434 | 64 |
| 10 | 4-methyl-2-pentanone | 552 | 68 |
| 11 | 2-ethylhexanal | 691 | 73 |

Example 12

Synthesis of 2,3-diisopropylidene succinic acid, diethyl ester

In a 1L jacketed reactor 264 mmol of acetone and 240 mmol of diethyl succinate were added to a mixture of 480 mmol of N,N-dimethylformanlide and 160 ml of toluene (solution A). In another 250 mL round bottom flask 240 mmol of potassium ethoxide were suspended in 60 mL of toluene (suspension B). The stirred suspension B was then added to solution A in 15 minutes at 60° C. The obtained mixture is stirred one hour at 60° C. Then, at 60° C, 276 mmol of ethylbromide were added dropwise in 15 minutes and the mixture stirred for six hours at 80° C. The temperature was then lowered to 60° C, 264 mmol of acetone and another batch of freshly prepared suspension B was added. The reaction mixture was stirred for 30 minutes at 60° C. After this period 276 mmol of ethylbromide were added in 15 minutes, and the obtained slurry stirred for 8 hours at 80° C. The reaction mixture was then allowed to cool to 10° C. and, after that, 120 mL of water were added. The organic layer was then separated and washed two times with 100 mL of water, the solvent evaporated to give 47 g of crude product isomers (77% of yield).

Comparison Example 1–2

Synthesis of 2-isopropylidene succinic acid, diethyl ester

The same procedure described in Example 5 was repeated with the difference that the solvent and the base reported in the table below were used

| | | Stobbe condensation | | | | Esterification | | |
|---|---|---|---|---|---|---|---|---|
| Ex. | Solvent | Base | T (° C.) | Time | Other | Yield | T (° C.) | Time |
| 1 | DMF | K₂CO₃ | 60 | 360' | EtOH (cat.) | — | — | — |
| 2 | i-PrOH | t-BuOK | 60 | 300' | | 32 | 60 | 600' |

DMF = N,N-dimethylformamide,
iPrOH = iso propanol,
tBuOK = potassium tert-butoxide.

What is claimed is:
1. A process for the preparation of succinates substituted with unsaturated hydrocarbon groups comprising: a step (a) carried out in the presence of a reaction medium and a base in which a compound of formula (I)

(I)

wherein R is a C1–C20 hydrocarbon group, $R^1$ is hydrogen or R, and $R^1$ and R can be linked together, with the proviso that when $R^1$ is hydrogen, R is a C4–C20 hydrocarbon group, is reacted with a compound of formula (II)

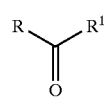

(I)

wherein R is a C1–C20 hydrocarbon group, $R^1$ is hydrogen or R, and $R^1$ and R can be linked together, with the proviso that when $R^1$ is hydrogen, R is a C4–C20 hydrocarbon group, is reacted with a compound of formula (II)

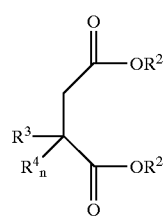

(II)

wherein $R^2$ is a C1–C20 hydrocarbon group, $R^3$ is hydrogen, a C1–C20 hydrocarbon group or an alkylidene group of formula $RR^1C=$, where R is a C1–C20 hydrocarbon group, $R^1$ is hydrogen or R, and $R^1$ and R can be linked together, with the proviso that when $R^1$ is hydrogen, R is a C4–C20 hydrocarbon group, $R^4$ is hydrogen or a C1–C20 hydrocarbon group, and n is 0 or 1, with the proviso that when $R^3$ is an alkylidene group of formula $RR^1C=$, n is 0; and a step (b) in which an unsaturated substituted product obtained in (a) is esterified; where said process step (a) is carried out under conditions such that (i) the compound of formula (II) is used in a molar amount substantially equal to, or lower than, the amount of compound (I), (ii) the base is used in a molar amount substantially equal to the compound of formula (II) and is selected from the group consisting of hydrides of formula $MeH_z$, and alkoxides of formula $R^5OMe$, wherein Me is a metal belonging to group I–II of the periodic table of elements, z is the valence of the metal and $R^5$ is a C1–C15 hydrocarbon group, and (iii) the reaction medium comprises an aprotic liquid medium or a protic liquid medium having a $K_a$, measured in water, lower than that of i-PrOH.

2. The process according to claim 1 in which the unsaturated hydrocarbon groups are alkylidene groups.

3. The process according to claim 1 in which the reaction medium is selected from aprotic diluents.

4. The process according to claim 3 in which the reaction medium is selected from the group consisting of toluene, ethylbenzene, xylene, dimethylformamide (DMF), N,N-dimethylacetamide, 1-methyl-2-pyrrolidone, diethylether and tetrahydrofurane.

5. The process according to claim 4 in which the reaction medium is dimethylformamide.

6. The process according to claim 1 in which the base comprises alkoxides of formula $R^5OMe$ where $R^5$ is a C1–C15 hydrocarbon group and Me is Na or K.

7. The process according to claim 6 in which the base is potassium tert-butoxide, sodium tert-butoxide, potassium ethoxide or sodium ethoxide.

8. The process according to claim 1 wherein R and R1 of formula (I) are C1–C20 hydrocarbon groups.

9. The process according to claim 8 in which R and $R^1$ are C1–C8 alkyl groups or alkylene groups linked together to form cyclic ketones.

10. The process according to claim 1 in which the esterification step (b) is carried out by contacting the alkylidene substituted product of step (a) with a compound of formula $R^6X$, where X is halogen and $R^6$ is C1–C20 hydrocarbon group.

11. The process according to claim 10 in which $R^6$ is the same as $R^2$.

12. The process according to claim 10 in which $R^6 X$ is ethyl bromide.

13. A process for the preparation of succinates substituted with unsaturated hydrocarbon groups comprising a step (a) carried out in the presence of a reaction medium and a base in which a compound of formula (I)

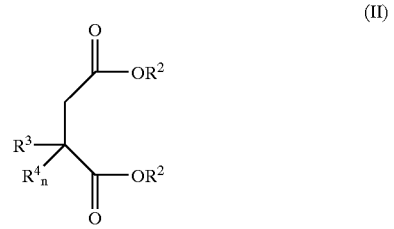

(II)

wherein $R^2$ is a C1–C20 hydrocarbon group, $R^3$ is hydrogen, a C1–C20 hydrocarbon group or an alkylidene group of formula $RR^1C=$, where R is a C1–C20 hydrocarbon group, $R^1$ is hydrogen or R, and $R^1$ and R can be linked together, with the proviso that when $R^1$ is hydrogen, R is a C4–C20 hydrocarbon group, $R^4$ is hydrogen or a C1–C20 hydrocarbon group, and n is 0 or 1, with the proviso that when $R^3$ is an alkylidene group of formula $RR^1 C=$, n is 0, and a step (b) in which an unsaturated substituted product obtained in (a) is esterified; where said process step (a) is carried out under conditions such that (i) the compound of formula (II) is used in a molar amount substantially equal to, or lower than, the amount of compound (I), (ii) the base is used in a molar amount substantially equal to the compound of formula (II) and is selected from the group consisting of hydrides of formula $MeH_z$ and alkoxides of formula $R^5OMe$, wherein Me is a metal beloning to group I–II of the periodic table of elements, z is the valence of the metal and $R^5$ is a C1–C15 hydrocarbon group, and (iii) the reaction medium comprises an aprotic liquid medium or a protic liquid medium having a $K_a$, measured in water, lower than that of i-PrOH wherein the succinates substituted with unsaturated hydrocarbon groups are alkylidene substituted succinic esters of formula (III):

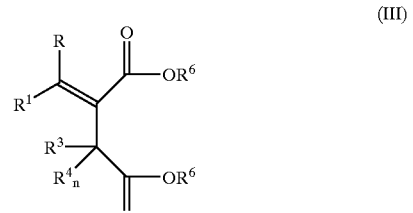

wherein $R^6$ is a C1–C20 hydrocarbon group.

14. The process according to claim 13 where in formula (III) n is 1 and both $R^3$ and $R^4$ are hydrogen.

15. The process according to claim 14 where in formula (II) of step (a) both $R^3$ and $R^4$ are hydrogen.

16. The process according to claim 15 wherein the reaction medium comprises DMF or toluene, and the base is EtOK, EtONa, t-BuOK or t-BuONa.

17. The process according to claim 13 wherein n is 0 and $R^3$ is an alkylidene group of formula $RR^1C=$.

18. The process according to claim 17 where after the completion of steps (a) and (b), an obtained monoalkylidene substituted succinate is subjected to an additional reaction step (a2) by contacting it, in the presence of a base, with an equal or higher molar amount of compound of formula (I) thereby obtaining a reaction product which is then subjected to an additional esterification step (b2).

19. The process according to claim 18 where in the starting compound of formula (II) of step (a), n is 1 and both $R^3$ and $R^4$ are hydrogen.

20. The process according to claim 19 in which the starting compound of formula (II) is diethyl succinate or diisobutyl succinate.

21. The process according to claim 18 where in step (a) the starting compound of formula (I) is selected from the group consisting of acetone, cyclohexanone and cyclopentanone.

22. The process according to claim 21 in which the compound of formula (I) is used in both step (a) and (a2).

23. The process according to claim 18 in which the base is selected from alkoxides of formula $R^5$OMe where $R^5$ is a C1–C15 hydrocarbon group and Me is Na or K.

24. The process according to claim 23 in which the base is selected from the group consisting of potassium tert-butoxide, sodium tert-butoxide, potassium ethoxide and sodium ethoxide.

25. The process according to claim 18 in which the reaction medium is the same in all the steps (a), (b), (a2) and (b2), and is DMF or toluene.

26. The process according to claim 18 wherein steps (a), (b), (a2) and (b2) are carried out in sequence without any intermediate separation step.

27. The process according to claim 1 further comprising catalytic hydrogenation of the succinates substituted with unsaturated hydrocarbon groups thereby producing alkyl substituted succinic esters.

28. The process according to claim 27 where the catalytic hydrogenation is carried out in the presence of a catalyst comprising palladium or platinum deposited on carbon.

* * * * *